(12) United States Patent
Matsumoto

(10) Patent No.: US 6,318,887 B1
(45) Date of Patent: Nov. 20, 2001

(54) BATTERY-POWERED LIGHT SOURCE ARRANGEMENT FOR ENDOSCOPE

(75) Inventor: Seiji Matsumoto, Nagano (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/365,771

(22) Filed: Aug. 3, 1999

(30) Foreign Application Priority Data

Aug. 21, 1998 (JP) .................................................. 10-235457

(51) Int. Cl.[7] .................................................. A61B 1/06
(52) U.S. Cl. ................................................ 362/574; 600/178
(58) Field of Search .................................. 362/574, 555, 362/545, 800, 247, 268; 600/101, 178; 313/512; 359/503

(56) References Cited

U.S. PATENT DOCUMENTS

| | | | |
|---|---|---|---|
| 3,938,177 | * 2/1976 | Hansen | 257/98 |
| 4,758,764 | * 7/1988 | Kuga | 313/499 |
| 4,803,992 | * 2/1989 | Lemelson | 600/242 |
| 4,831,429 | * 5/1989 | Nikashima | 257/55 |
| 5,471,023 | * 11/1995 | Kaizu | 200/310 |
| 5,813,403 | * 9/1998 | Soller | 600/310 |
| 5,925,898 | * 7/1999 | Spath | 257/98 |
| 6,110,106 | * 8/2000 | MacKinnon | 600/181 |

* cited by examiner

Primary Examiner—Alan Cariaso
Assistant Examiner—Hargobind S. Sawhney
(74) Attorney, Agent, or Firm—Young & Thompson

(57) ABSTRACT

A light source arrangement for a battery-powered light source unit of an endoscope comprises an optically transparent base board, a single light emitting element such as a bare LED arranged at the center of and in close proximity to the back of the transparent base board or a plurality of light emitting elements such as bare LEDs arranged in close proximity to the back of the transparent base board at regular angular intervals and regular distances from the center of the transparent base board, and a reflector disposed behind the transparent base board so as to reflect light emanating backward from the light emitting element or elements toward the transparent base board.

10 Claims, 3 Drawing Sheets

BATTERY-POWERED LIGHT SOURCE ARRANGEMENT FOR ENDOSCOPE

BACKGROUND OF THE INVENTION

1. Field of the Invention

This invention relates to a light source for an endoscope, and, in particular, to a light source arrangement for a battery-powered light source unit for an endoscope.

2. Description of Related Art

Typically, light source units are used to illuminate the inside of an organ of a human body while the inside of the organ is observed by, for example, an electronic endoscope. Such a light source unit is equipped with a lamp such as a halogen lamp and a xenon lamp as a light source. Light from the lamp is introduced into a light guide of the electronic endoscope to an illumination window and applied to a location to be observed and video displayed.

The light source, e.g. the halogen lamp and the xenon lamp, is energized by commercial power supply because it consumes electric power to somewhat significant extent. In view of less electric power consumption as well as miniaturization and lightening for portability, it is desired for the light source unit to use a battery-powered light source arrangement. In the field of electronic endoscope and information processing machines, miniaturization and electric power reduction of the battery-powered light source unit are advanced in regard to electronic circuits and, on the other hand, make very slow progress in regard to light source units due to utilization of a halogen lamp or a xenon lamp which ensures a somewhat great amount of light.

SUMMARY OF THE INVENTION

It is therefore an object of the invention to provide a light source arrangement for a battery-powered light source unit for an endoscope which realizes miniaturization lightening for portability and electric power reduction of the battery-powered light source unit.

The foregoing object of the invention is accomplished by providing a light source arrangement for a battery-powered light source unit of an endoscope which has an illumination system. The light source arrangement comprises an optically transparent base board, light emitting means, for example a single bare light emitting element or a plurality of bare light emitting elements, arranged in close proximity to the back of the transparent base board, and a reflector disposed behind the transparent base board so as to reflect light emanating backward from the light emitting means toward the transparent base board.

In a preferred embodiment of the invention, the light source arrangement further comprises a power supply circuit printed on the back of the transparent base board and transparent electric conductive lead wires for connecting the light emitting means to the power supply circuit such as a patterned film of tin oxide ($SnO_2$) and a patterned film of indium oxide ($In_2O_3$) which have low specific resistances.

According to the light source arrangement of the invention in which a single bare light emitting diode or a plurality of bare light emitting diodes are employed, light emanating from the bare light emoting diode or diodes are partly directed directly forward and partly directed backward and reflected by the reflector. Accordingly, almost entire amount of light emanating from the bare light emitting diode or the bare light emitting diodes are directed to the transparent base board, so that the light pass through the transparent base board are efficiently collected by the focusing lens and directed to the light guide. The utilization of a patterned film of tin oxide ($SnO_2$) or a patterned film of indium oxide ($In_2O_3$) as the conductive lead wires for connecting the light emitting element to the power supply circuit resistances eliminates a loss of light. Further, the utilization of a plurality of bare light emitting diodes provides a large amount of light and realizes a battery-powered light source unit.

BRIEF DESCRIPTION OF THE DRAWINGS

The above and other objects and features of the present invention will be understood from the following description of a specific embodiment thereof when considering in conjunction with the accompanying drawings, in which same or similar parts are denoted by the same reference numerals throughout the drawings, and where.

DETAILED DESCRIPTION OF THE SPECIFIC EMBODIMENT

Figure 1:
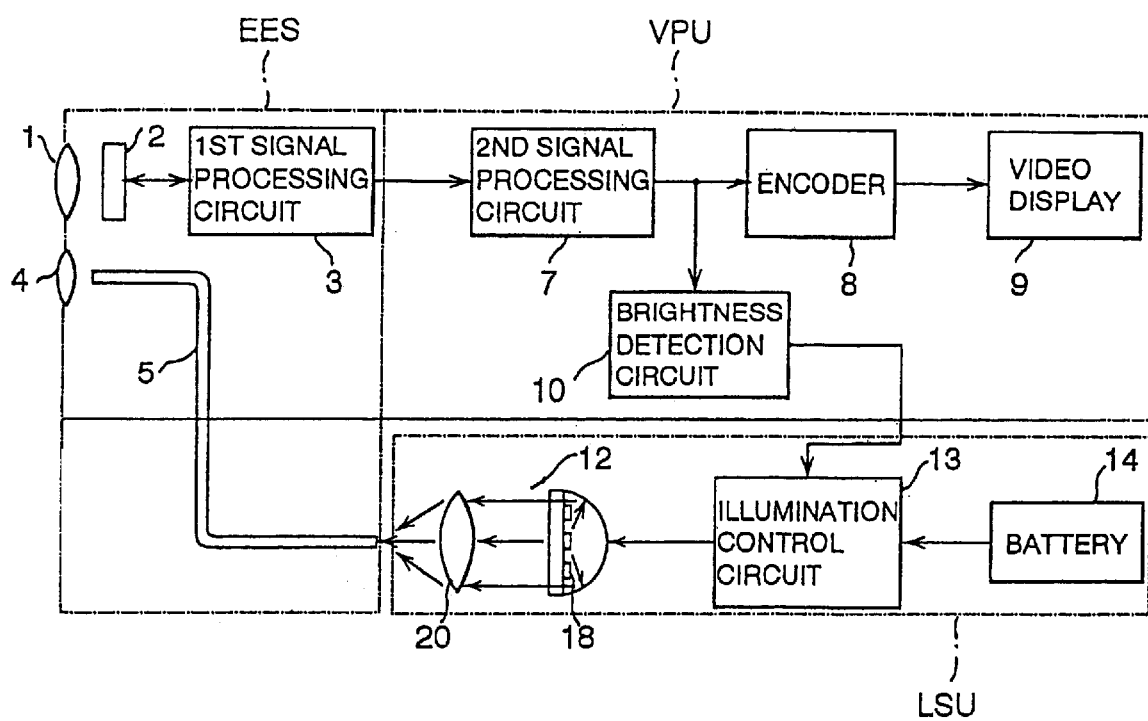
FIG. 1 is a schematic illustration of an electronic endoscope in which a battery-powered light source unit is provided with a light source arrangement of the invention.

Referring to the drawings in detail and, in particular, to FIG. 1 schematically showing an electronic endoscope system which comprises an electronic endoscope EES, a video processing machine VPM and a battery-powered light source unit LSU of the invention, the electronic endoscope EES has a video producing system including an imaging lens 1, a solid-state imaging device such as a charge coupled device (CCD) 2 on which an optical image is projected by the imaging lens 1, and a first signal processing circuit 3 and an illumination system including a light projection lens 4 and a light guide 5. Video signal provided by the CCD 2 is sent to the first signal processing circuit 3 for signal amplification. The light projection lens 4 projects illumination light which is introduced into the light guide 5 to illuminate an internal location of a human organ to be observed and/or video displayed. The video processing machine VPM comprises a second signal processing circuit 7, an encoder 8, a brightness detection circuit 10 and a video display 9. The video signal amplified in the first signal processing circuit 3 is sent to the second signal processing circuit 7 and subjected to gamma processing and the like therein. The video signal is finally sent to the video display 9 through the encoder 8. The brightness detection circuit 10 detects brightness of an optical image based on the video signal from the second signal processing circuit 7 and generates a signal representative of the brightness of an optical image. The battery-powered light source unit LSU comprises a light source arrangement 12 including a single or a plurality of bare light emitting diodes (LEDs) 18 (see FIG. 2A or 3A), a focusing lens 22, an illumination control circuit 13 and a battery 14. The bare LEDs 18 of the light source arrangement 12 are powered by the battery 14 to produce light. The light emanating from the light source arrangement 12 is controlled in intensity according to the brightness signal by the illumination control circuit 13 and focused upon the incident end of the light guide 5 of the electronic endoscope EES by the focusing lens 22. The battery 14 may be used to power the entire electronic endoscope system.

Figure 2A:
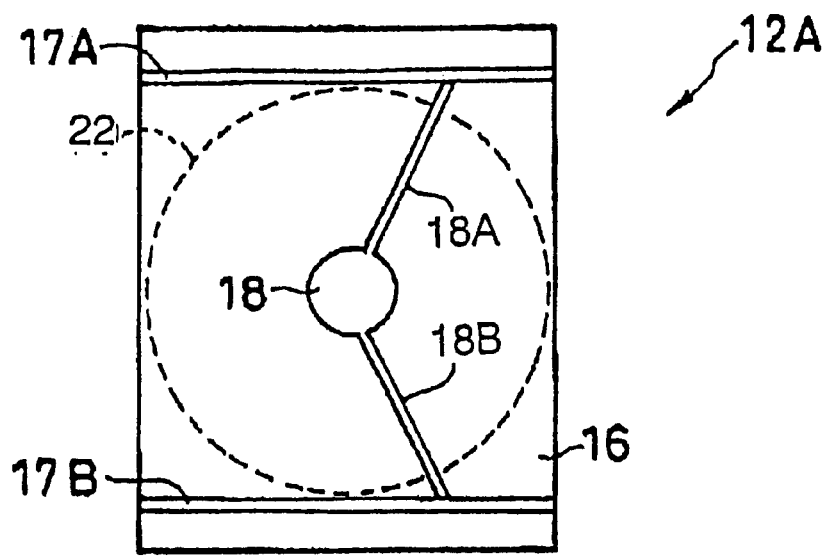
FIG. 2A is a cross-sectional view of a light source arrangement in accordance with a preferred embodiment of the invention.
Figure 2B:
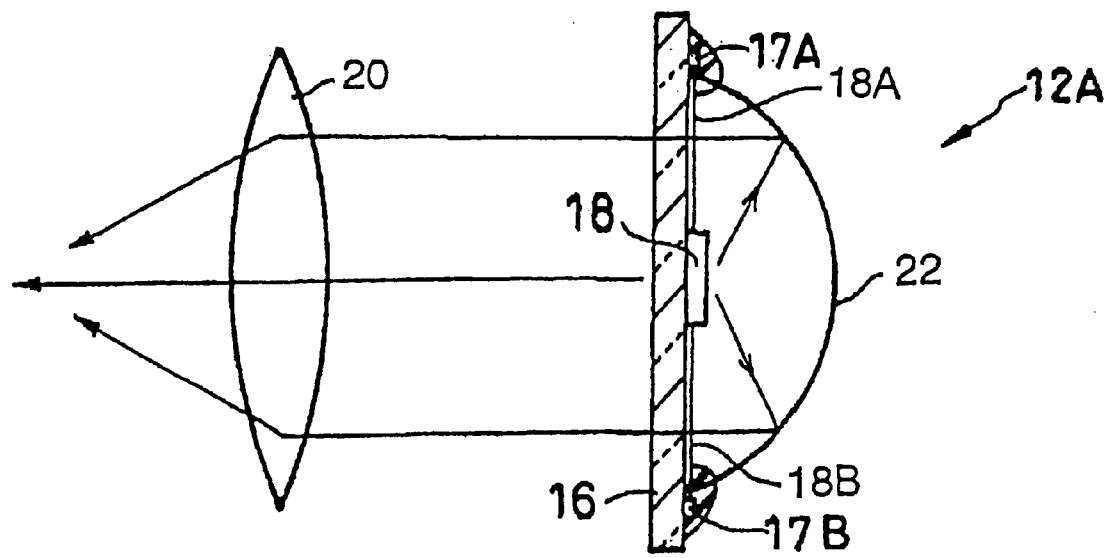
FIG. 2B is a rear view of a transparent base board of the light source arrangement shown in FIG. 2A.

FIGS. 2A and 2B show a light source arrangement 12A in accordance with a preferred embodiment of the invention. The light source arrangement 12A comprises an optically transparent base board 16, a wiring including a pair of power lines 17A and 17B printed on the back of the transparent base board 16 along opposite sides of the transparent base board 16, and a bare LED 18 attached to the back of the transparent base board 16 at the center of the transparent base board 16 and is connected to the power lines 17A and 17B by lead lines 18A and 18B such as conventional thin electric wires, or preferably transparent electric conductive wires having a low specific resistance such as a patterned film of tin oxide ($SnO_2$) and a patterned film of indium oxide ($In_2O_3$), respectively. A reflector 20 having a spherical surface or a parabolic surface is attached to the back of the transparent base board 16 so as to reflect light emanating backward from the bare LED 18 and direct them toward the transparent base board 16.

The bare LED 18 emits light when energized with a voltage supplied from the battery 14. The light from the bare LED 18 travel partly directly and partly after reflection by the reflector 20 toward the focusing lens 22 passing through the transparent base board 16 and then are focused upon the incident end of the light guide 5 of the electronic endoscope EES by the focusing lens 22. The focused light, which has a predetermined intensity at the incident end of the light guide 5, is transmitted through the light guide 5 and directed onto an internal location of a human organ by the light projection lens 4 as shown in FIG. 1. An optical image of the internal location is formed on the CCD 2 by the imaging lens 1. Video signal from the CCD 2 is processed by the first and second signal processing circuits 3 and 7 and transferred to the video display 9 through the encoder 8 for display of a visual video image on a screen. Simultaneously, the video signal is transferred to the brightness detection circuit 10 which detects brightness of the optical image and generates a signal indicative of the image brightness. The illumination control circuit 13 controls the energizing voltage supplied to the bare LED 18 according to the brightness of the optical image to vary the intensity of light from the bare LED 18. Specifically, for example, the illumination control circuit 13 boosts the energizing voltage when the optical image has a brightness lower than a specified level or drops it when having a brightness higher than the specified level. The illumination control circuit 13 may be designed and adapted such that it variably controls the duration time of energization of the bare LED 18 so as thereby to change a charge storage time for which the bare LED 18 is permitted to store charges.

Figure 3A:
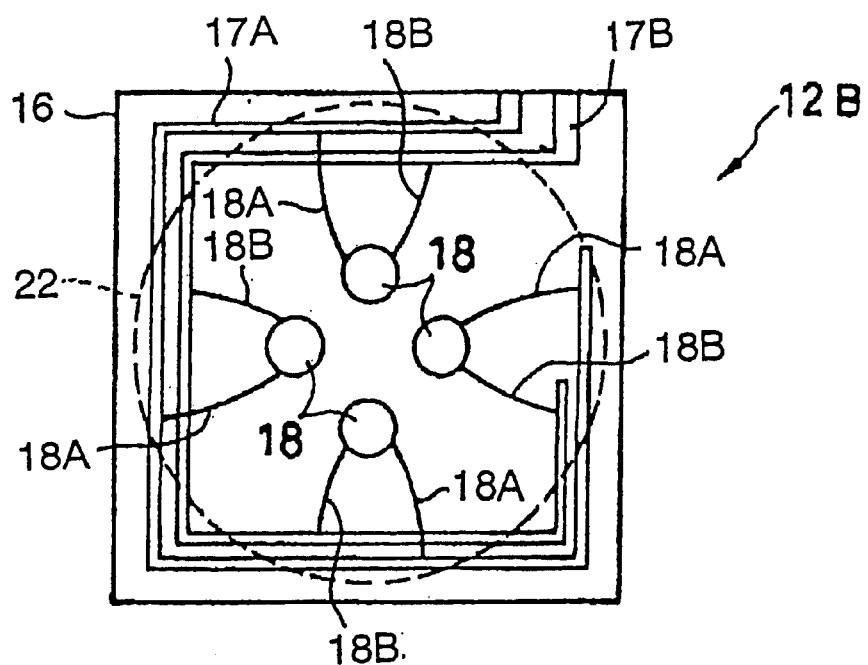
FIG. 3A is a cross-sectional view of a light source arrangement in accordance with another preferred embodiment of the invention.
Figure 3B:
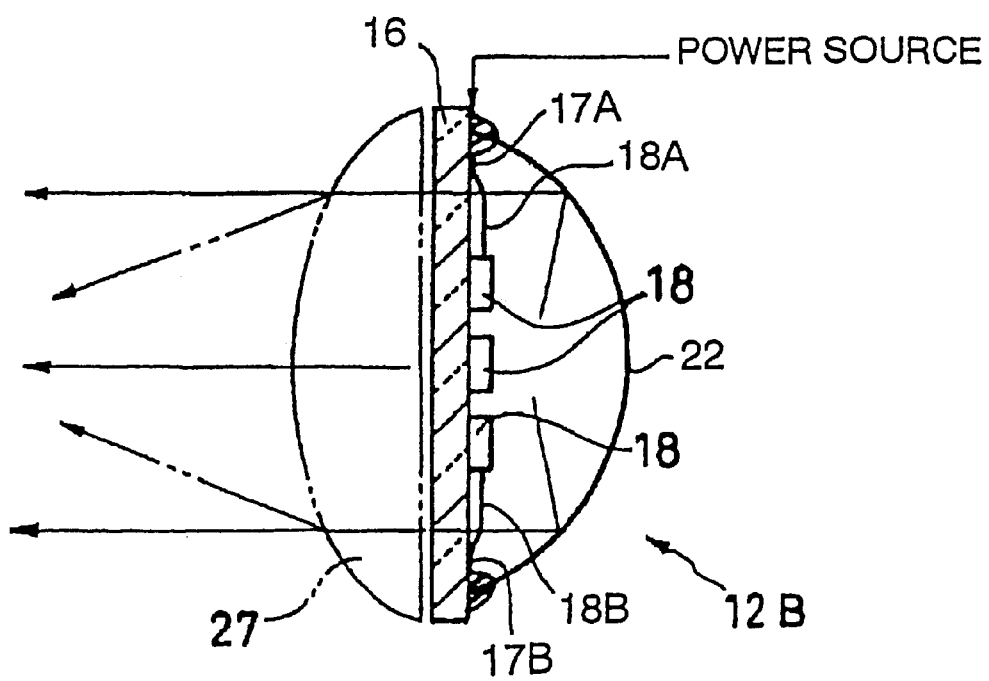
FIG. 3B is a rear view of a transparent base board of the light source arrangement shown in FIG. 3A.

FIGS. 3A and 3B show a light source arrangement 12B in accordance with another preferred embodiment of the invention. The light source arrangement 12B comprises an optically transparent base board 16, a wiring including a pair of power lines 17A and 17B printed on the back of the transparent base board 16 along approximately all sides of the transparent base board 16, and a plurality of, for example four in this embodiment, bare LEDs 18 fixedly arranged on the back of the transparent base board 16 at regular intervals and regular distances from the center of the transparent base board 16 and is connected to the power lines 17A and 17B by lead lines 18A and 18B preferably such as transparent electric conductive wires having a low specific resistance such as a patterned film of tin oxide ($SnO_2$) and a patterned film of indium oxide ($In_2O_3$), respectively. A reflector 20 having a spherical surface or a parabolic surface is attached to the back of the transparent base board 16 so as to reflect light emanating backward from the bare LEDs 18 and direct them toward the transparent base board 16.

In the same manner as described as to the previous embodiment, light emanating from the bare LEDs 18 travel partly directly and partly after reflection by the reflector 20 toward the focusing lens 22 (see FIG. 2) passing through the transparent base board 16 and then are focused upon the incident end of the light guide 5 of the electronic endoscope EES by the focusing lens 22. The focused light beam, which has a predetermined intensity at the incident end of the light guide 5, is transmitted through the light guide 5 and directed onto an internal location of a human organ by the light projection lens 4 as shown in FIG. 1. An optical image of the internal location is formed on the CCD 2 by the imaging lens 1. Video signal from the CCD 2 is processed by the first and second signal processing circuits 3 and 7 and transferred to the video display 9 through the encoder 8 for display of an visual video image on a screen. Simultaneously, the video signal is transferred to the brightness detection circuit 10 which detects brightness of the optical image and generates a signal indicative of the image brightness. The illumination control circuit 13 controls the energizing voltage supplied to the bare LEDs 18 according to the brightness of the optical image to vary the intensity of light from the bear LEDs 18.

In both embodiments described above, the illumination control circuit 13 may be designed and adapted such that it variably controls the duration time of energization of the bare LED 18 or bare LEDs 18 so as thereby to change a charge storage time for which the CCD 2 is permitted to store charges. In the second embodiment, the bare LEDs 18 may be arranged in a straight row. Further, as shown by a double dotted line in FIG. 3A, a condenser 27 may be installed in front of the transparent base board 16.

According to the battery-powered light source unit LSU thus constructed, the utilization of a single bare LED or a plurality of bare LEDs 18, which consume only small electric power and is energized by the battery 14, in the light source arrangement 12A, realizes less electric power consumption and miniaturization and lightening for portability of the battery-powered light source unit LSU. The reflector provides efficient reflection of light emanating backward from the bare LED 18 or the bare LEDs 18. In particular, the utilization of a plurality of bare LEDs 18 and/or the condenser lens 27 provides a significantly increased intensity of light introduced into the light guide 5.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. A light source arrangement for a battery-powered light source unit of an endoscope which has an illumination system, comprising:

an optically transparent base board;

at least one light source arranged in close proximity to a rear surface of said transparent base board;

first and second power lines disposed on the rear surface of the transparent base board so that each of the first and second power lines substantially surrounds the at least one light source;

a first and second lead line for each said light source, each said first lead line electrically connecting the first power line to a respective said light source, and each said second lead line electrically connecting the second power line to a respective said light source; and a reflector disposed behind said transparent base board so as to reflect light emanating backward from said at least one light source toward said transparent base board.

2. A light source arrangement as defined in claim 1, wherein the first and second lead lines are transparent.

3. A light source arrangement as defined in claim 2, wherein said transparent electric conductive lead wires comprise one of a patterned film of tin oxide ($SnO_2$) and a patterned film of indium oxide ($In_2O_3$).

4. A light source arrangement as defined in claim 1, wherein said at least one light source comprises a single bare light emitting diode.

5. A light source arrangement as defined in claim 4, and further comprises a condenser lens disposed in front of said transparent base board.

6. A light source arrangement as defined in claim 1, wherein said at least one light source comprises a plurality of bare light emitting diodes arranged at regular angular intervals and regular distances from a center of said transparent base board.

7. A light source arrangement as defined in claim 6, and further comprises a condenser lens disposed in front of said transparent base board.

8. The light source arrangement of claim 1, wherein each said lead line is transparent, and wherein at least one said lead line is arranged so that it passes over one of the first and second power lines without contacting either the power line being crossed or the transparent base board.

9. The light source arrangement of claim 1, wherein at least one said lead line is arranged so that it passes over one of the first and second power lines without contacting either the power line being crossed or the transparent base board.

10. An endoscope comprising:
   a battery;
   an imaging lens;
   a charge coupled device adapted to receive an image formed by the objective lens;
   a signal processing circuit connected to receive an output of the charge coupled device;
   an encoder adapted to receive an output of the signal processing circuit;
   a video display adapted to receive an output of the encoder;
   a light source arrangement comprising:
      an optically transparent base board;
      at least one light source arranged in close proximity to a rear surface of said transparent base board;
      first and second power lines disposed on the rear surface of the transparent base board so that each of the first and second power lines substantially surrounds the at least one light source;
      a first and second lead line for each said light source, each said first lead line electrically connecting the first power line to a respective said light source, and each said second lead line electrically connecting the second power line to a respective said light source; and
      a reflector disposed behind said transparent base board so as to reflect light emanating backward from said at least one light source toward said transparent base board;
   wherein the battery provides power to the entire endoscope.

* * * * *